United States Patent [19]

Walker et al.

[11] Patent Number: 4,940,712

[45] Date of Patent: Jul. 10, 1990

[54] DERIVATIVES OF HYDROXYPRIMIDINES AS LEUKOTRIENE SYNTHESIS INHIBITORS

[75] Inventors: Frederick J. Walker, Preston; Lawrence S. Melvin, Ledyard, both of Conn.

[73] Assignee: Pfizer Inc., New York, N.Y.

[21] Appl. No.: 358,032

[22] Filed: May 26, 1989

[51] Int. Cl.$^5$ .................. A61K 31/505; C07D 239/47; C07D 239/56; C07D 401/04

[52] U.S. Cl. ..................................... 514/272; 514/269; 514/273; 514/274; 514/826; 514/863; 544/298; 544/316; 544/318

[58] Field of Search .............. 544/298, 316, 318, 330, 544/331, 332; 514/272, 275, 269, 273, 274

[56] References Cited

U.S. PATENT DOCUMENTS

| | | | |
|---|---|---|---|
| 3,499,898 | 3/1970 | von Bebenburg | 544/332 |
| 4,554,276 | 11/1985 | La Mattina | 514/272 |
| 4,711,888 | 12/1987 | Walker et al. | 514/269 |

FOREIGN PATENT DOCUMENTS 2045756  11/1980  United Kingdom .

OTHER PUBLICATIONS

La Mattina et al., Chem. Abst. 106:138466j.
Bray et al., Biochem. J., 48, 400 (1951).
Dubovenko et al., Chemical Abstracts, 94, Abstract No. 1214462z (1981).
Chesterfield et al., J. Chem. Soc., 4595 (1960).
Hull, "Synthesis of 5-hydroxypyrimidines", Chemical Abstracts, 51, 3, Abstract No. 1979 (f), (1957).

*Primary Examiner*—Cecilia Shen
*Attorney, Agent, or Firm*—Peter C. Richardson; Paul H. Ginsburg; Karen DeBenedictis

[57] ABSTRACT

2-Amino and 2-thio-4-substituted-5-(hydroxy or alkoxy)-pyrimidines, which may be 6-substituted, and derivatives thereof are disclosed. The compounds are inhibitors of leukotriene synthesis and are, therefore, useful for the treatment of pulmonary, inflammatory, dermatological, allergic and cardiovascular diseases. The compounds are also cytoprotective and therefore, useful in the treatment of peptic ulcers.

23 Claims, No Drawings

DERIVATIVES OF HYDROXYPRIMIDINES AS LEUKOTRIENE SYNTHESIS INHIBITORS

BACKGROUND OF THE INVENTION

This invention relates to hydroxy and alkoxy substituted pyrimidines, more particularly, 2-amino 2-thio, 2-substituted amino and 2-substituted thio-4-substituted-5-(hydroxy or alkoxy) pyrimidines which are optionally 6-substituted, acyl derivatives thereof pharmaceutical compositions containing such compounds as active ingredients and methods of treatment with such compounds. Some hydroxy compounds from which the compounds of the present invention may be prepared and that are inhibitors of leukotriene synthesis are disclosed in European Patent Application publication No. 210 044.

Bray et al., in Biochem. J., 48, 400 (1951), describe 2-amino-4,6-dimethyl-5-hydroxypyrimidine and its preparation without disclosing any pharmaceutical or other utility.

Dubovenko et al., in Chemical Abstracts, 94: 121446z (1981), describe 2-dimethylamino-4,6-diphenyl-5-hydroxypyrimidine and its preparation without disclosing any pharmaceutical or other utility.

Chesterfield et al., in J. Chem. Soc., 4595, (1960), describe 4,6-dimethyl-5-hydroxy-2-thiopyrmidine and its preparation without disclosing any pharmaceutical or other activity.

Esanu et al., in U.K. Patent Application No. 2045756, disclose 2-isopropylamino-5-hydroxypyrimidine for the treatment of muscular dystrophy. This prior-published application does not disclose any substitution of the mentioned compound at the 4-and 6-positions of the pyrimidine group.

LaMattina, in U.S. Pat. No. 4,554,276, assigned to the same assignee as the present application, discloses 2-amino-4-methyl-5-hydroxypyrimidines having similar pharmaceutical utilities as the compounds of the present invention.

Walker et al., in U.S. Pat. No. 4,711,888, assigned to the same assignee as the present application, disclose 2-amino-4 substituted-5-(hydroxy or alkoxy)-pyrimidines, which may be 6-substituted, and derivatives thereof having similar pharmaceutical activities as the compounds of the present invention.

Walker et al., in PCT Application PCT/US 87/03171, filed Dec. 2, 1987 and also assigned to the same assignee as the present application, disclose acyl derivatives of 2-amino-4-substituted-5-hydroxy pyrimidines, which may be 6-substituted, and derivatives thereof having similar pharmaceutical activities as the compounds of the present invention.

Current treatment of asthma focuses on the relief of acute bronchospasm through the use of bronchodilators. It is thought that acute bronchospasm is only an overt manifestation of chronic inflammation. Leukotrienes may play a role both in the bronchospasm and the chronic inflamation. They are known to be potent vasodilators and chemotactic agents. They are also produced in allergic reactions and bring about slow contraction of lung tissue in vitro. An inhibitor of leukotriene synthesis should therefore be of use in the treatment of asthma and other pulmonary diseases.

Chronic gastric and duodenal ulcers, together known as peptic ulcers, are the subject of a variety of treatments, including special diets, drug therapy and surgery, depending upon the severity of the condition. Particularly valuable therapeutic agents useful for the treatment of gastric hyperacidity and peptic ulcers are the histamine-$H_2$ receptor antagonists, which block the action of the physiologically-active compound histamine at the $H_2$-receptor sites in the animal body and thereby inhibit the secretion of gastric acid.

SUMMARY OF THE INVENTION

The present invention relates to compounds of the formula

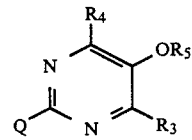

wherein Q is $R_1R_2N-$ or $SO_nR_{10}$, wherein n is an integer from 0 to 2: $R_1$ is hydrogen, $(C_1-C_{15})$alkyl, $(C_1-C_{15})$alkyl - $(C_3-C_8)$cycloalkyl, $(C_2-C_{15})$alkenyl - $(C_3-C_8)$cycloalkenyl, $(C_2-C_{15})$alkynyl - $(C_3-C_8)$ cycloalkyl, $(C_3-C_{15})$alkynyl, a heteroaryl containing group selected from heteroaryl - $(C_1-C_{10})$alkyl, heteroaryl - $(C_1-C_{10})$ alkenyl, and heteroaryl - $(C_1-C_{10})$alkynyl, wherein the heteroaryl moiety is selected from the group consisting of thiophene and furane, $(C_7-C_{20})$-phenylalkenyl, substituted $(C_7-C_{20})$phenylalkenyl, $(C_7-C_{12})$phenylalkynyl, substituted $(C_7-C_{20})$-phenylalkynyl, $(C_1-C_6$ alkoxy) - $(C_2-C_6)$alkyl, phenoxy -$(C_2-C_6)$alkyl, substituted phenoxy -$(C_2-C_6)$alkyl, $(C_1-C_6)$alkoxy- $(C_2-C_6)$alkenyl, $(C_1-C_6)$alkoxy - $(C_2-C_6)$alkynyl, phenoxy -$(C_2-C_6)$alkenyl, substituted phenoxy- $(C_2-C_6)$alkenyl, phenoxy -$(C_2-C_6)$alkynyl, substituted phenoxy- $(C_7-C_{12})$alkynyl, or $(C_7-C_{12})$phenylalkyl- $(C_7-C_{12})$phenylalkyl: $R_2$ is hydrogen, $(C_1-C_{15})$alkyl, cyclopentyl, cyclohexyl, $(C_3-C_{15})$alkenyl, phenyl, substituted phenyl, $(C_7-C_{20})$phenylalkyl, substituted $(C_7-C_{20})$phenylalkyl or $(C_3-C_8)$cycloalkyl -$(C_1-C_{15})$alkyl: or $R_1$ and $R_2$ together with the nitrogen atom to which they are attached form a pyrrolidinyl or piperidyl group which may be substituted by one $(C_1-C_6)$alkyl, phenyl or $(C_7-C_{20})$-phenylalkyl; $R_3$ and $R_4$ are independently selected from the group consisting of hydrogen, $(C_1-C_6)$alkyl, phenyl, substituted phenyl, $(C_7-C_{20})$phenylalkyl, substituted $(C_7-C_{20})$phenylalkyl, furyl, thienyl, furyl substituted by one $(C_1-C_3)$alkyl, thienyl substituted by one $(C_1-C_3)$alkyl, $(C_1-C_6)$alkyl substituted with carbonyl, chloro, fluoro, bromo, iodo, trifluoromethyl, hydroxy, or $(C_1-C_3)$alkoxy, $(C_2-C_6)$alkenyl, $(C_2-C_6)$alkynyl, $(C_3-C_6)$cycloalkyl, $(C_1-C_{15})$alkyl -$(C_3-C_8)$cycloalkyl, $(C_2-C_{15})$alkenyl - $(C_3-C_8)$cycloalkyl, or $(C_2-C_{15})$-alkynyl- $(C_3-C_8)$cycloalkyl: $R_5$ is $-COR_6$, $-CH(CH_3)OCOOR_{11}$, $-CH_2OCOOR_{11}$ or $R_7$; $R_6$ is hydrogen, $(C_1-C_{10})$ alkyl, $(C_1-C_{10})$alkoxy, phenyl, substituted phenyl, $(C_7-C_{20})$-phenylalkyl, substituted $(C_7-C_{20})$-phenylalkyl, $(C_2-C_3)$alkylcarboxy, $-NR_8R_9$, wherein $R_8$ and $R_9$ are independently selected from the group consisting of $(C_1-C_{10})$ alkyl, phenyl, substituted phenyl, $(C_7-C_{20})$phenylalkyl and substituted $(C_7-C_{20})$-phenylalkyl; $R_7$ is hydrogen or $(C_1-C_6)$alkyl: $R_{10}$ is $(C_5-C_{15})$alkyl, $(C_5-C_{15})$alkenyl, phenyl, substituted phenyl, $(C_7-C_{20})$phenylalkyl, substituted $(C_7-C_{20})$-phenylalkyl, $(C_7-C_{20})$phenylalkyl-$(C_7-C_{20})$phenylalkyl, $(C_1-C_{17})$alkyl- $(C_3-C_8)$cycloalkyl, $(C_2-C_{17})$alkenyl($C_3-C_8)$cycloalkyl, $(C_2-C_{17})$alkynyl- $(C_3-C_8)$cycloalkyl, $(C_5-C_{15})$alkynyl, a heteroaryl containing group selected from heteroaryl- $(C_1-C_{10})$alkyl, heteroaryl($C_1$-$C_{10}$)alkenyl, and heteroaryl-($C_1$-$C_{10}$)alkynyl, wherein the heteroaryl moiety is selected from the group consisting of thiophene and furane, ($C_7$-$C_{20}$)phenylalkenyl, substituted ($C_7$-$C_{20}$)phenylalkenyl, ($C_7$-$C_{20}$)phenylalkynyl, substituted ($C_7$-$C_{20}$)phenylalkynyl, ($C_1$-$C_6$)alkoxy- ($C_4$-$C_6$)alkyl, phenoxy- ($C_2$-$C_6$)alkyl, substituted phenoxy- ($C_2$-$C_6$)alkyl, ($C_1$-$C_6$)alkoxy- ($C_3$-$C_6$)alkenyl, ($C_1$-$C_6$)alkoxy-($C_3$-$C_6$)alkynyl, phenoxy- ($C_3$-$C_6$)alkenyl, substituted phenoxy- ($C_3$-$C_6$)alkenyl, phenoxy- $C_3$-$C_6$(alkynyl), or substituted phenoxy- ($C_3$-$C_6$)alkynyl: wherein the phenyl moieties on said substituted phenyl, said substituted phenylalkyl, said substituted phenylalkenyl, said substituted phenylalkylnyl, and said substituted phenoxy may be substituted by one or two moieties selected from the group consisting of fluoro, chloro, bromo, iodo, hydroxy, ($C_1$-$C_3$)alkyl, ($C_1$-$CF_3$)alkoxy and $CF_3$; and $R_{11}$ is ($C_1$-$C_4$)alkyl: with the proviso that when $R_1$ and $R_2$ are both hydrogen, $R_6$ cannot be methyl, with the proviso that when Q is $R_1R_2N$—, $R_7$ is hydrogen and $R_3$ is ($C_1$-$C_6$)alkyl, then $R_4$ is not hydrogen, and with the proviso that when Q is $R_1R_2N$— and $R_1$ is hydrogen or ($C_1$-$C_{15}$)alkyl, $R_2$ is not hydrogen, ($C_1$-$C_{15}$)alkyl, cyclopentyl, cyclohexyl, ($C_3$-$C_{15}$)alkenyl, phenyl, or ($C_7$-$C_{20}$)phenylalkyl which may be substituted in the phenyl by one or two of fluoro, chloro, ($C_1$-$C_3$)alkyl, ($C_1$-$C_3$)alkoxy, or $CF_3$; and with the proviso that when Q is $R_1R_2N$—, $R_3$ and $R_4$ are not both hydrogen: a pharmaceutically acceptable acid addition salt thereof, or, when $R_6$ is ($C_2$-$C_3$)alkylcarboxy or $R_7$ is hydrogen, a pharmaceutically acceptable base addition salt thereof One embodiment of the present invention relates to compounds of the formula I wherein $R_5$ is —$COR_6$ and Q is $R_1R_2N$—, wherein $R_1$ is hydrogen, ($C_1$-$C_{15}$)alkyl, ($C_1$-$C_{15}$)alkyl-($C_3$-$C_8$)cycloalkyl, ($C_2$-$C_{15}$)alkenyl-($C_3$-$C_8$)cycloalkyl, ($C_2$-$C_{15}$)alkynyl-($C_3$-$C_8$)cycloalkyl, ($C_3$-$C_{15}$)alkynyl, a heteroaryl contain selected from heteroaryl-($C_1$-$C_{10}$)alkyl, heteroaryl-($C_1$-$C_{10}$)alkenyl, and heteroaryl-($C_1$-$C_{10}$)-alkynyl, wherein the heteroaryl moiety is selected from the group consisting of thiophene and furane, ($C_7$-$C_{20}$)phenylalkenyl, substituted ($C_7$-$C_{20}$)phenylalkenyl, ($C_7$-$C_{20}$)phenylalkynyl, substituted ($C_7$-$C_{20}$)phenylalkynyl, ($C_1$-$C_6$) alkoxy-($C_2$-$C_6$)alkyl, phenoxy-($C_2$-$C_6$)alkyl, substituted phenoxy-($C_2$-$C_6$)alkyl, ($C_1$-$C_6$)alkoxy-($C_2$-$C_6$)alkenyl, ($C_1$-$C_6$)alkoxy-($C_2$-$C_6$)alkynyl, phenoxy-($C_2$-$C_6$)alkenyl, substituted phenoxy-($C_2$-$C_6$)alkenyl, phenoxy-($C_2$-$C_6$)-alkynyl, substituted phenoxy-($C_2$-$C_6$)alkynyl, or ($C_7$-$C_{12}$)phenylalkyl-($C_7$-$C_{12}$)phenylalkyl: $R_2$ is hydrogen, ($C_1$-$C_{15}$)alkyl, cyclopentyl, cyclohexyl, ($C_3$-$C_{15}$)alkenyl, phenyl, substituted phenyl, ($C_7$-$C_{20}$)phenylalkyl, substituted ($C_7$-$C_{20}$)phenylalkyl or ($C_3$-$C_8$)-cycloalkyl-($C_1$-$C_{15}$)alkyl; or $R_1$ and $R_2$ together with the nitrogen atom to which they are attached form a pyrrolidinyl or piperidyl group which may be substituted by one ($C_1$-$C_6$)alkyl, phenyl or ($C_7$-$C_{20}$)phenylalkyl; $R_3$ is ($C_1$-$C_6$)alkyl, phenyl, substituted phenyl, ($C_7$-$C_{20}$)phenylalkyl, substituted ($C_7$-$C_{20}$)phenylalkyl, furyl, thienyl, furyl substituted by one ($C_1$-$C_3$)alkyl, thienyl substituted by one $C_1$-$C_3$alkyl, ($C_1$-$C_6$)alkyl substituted with carbonyl, chloro, fluoro, bromo, iodo, trifluoromethyl, hydroxy or ($C_1$-$C_3$)alkoxy, ($C_2$-$C_6$)alkenyl, ($C_2$-$C_6$)alkynyl, ($C_3$-$C_6$)cycloalkyl, ($C_1$-$C_{15}$)-alkyl-($C_3$-$C_8$)cycloalkyl, ($C_2$-$C_{15}$)alkenyl-($C_3$-$C_8$)cycloalkyl, or ($C_2$-$C_{15}$)alkynyl-($C_3$-$C_8$)cycloalkyl; $R_4$ is hydrogen, ($C_1$-$C_6$)alkyl, phenyl substituted phenyl, ($C_7$-$C_{20}$)phenylalkyl, or substituted ($C_7$-$C_{20}$)phenylalkyl; and $R_6$ is hydrogen, ($C_1$-$C_{10}$) alkyl, ($C_1$-$C_{10}$)alkoxy, phenyl, substituted phenyl, ($C_7$-$C_{20}$)phenylalkyl, substituted ($C_7$-$C_{20}$)phenylalkyl, ($C_2$-$C_3$)alkylcarboxy, —$NR_8R_9$, wherein $R_8$ and $R_9$ are independently selected from the group consisting of ($C_1$-$C_{10}$)alkyl, phenyl, substituted phenyl, ($C_7$-$C_{20}$)phenylalkyl and substituted ($C_7$-$C_{20}$)phenylalyl; wherein the phenyl moieties on said substituted phenyl, said substituted phenylalkyl, said substituted phenylalkenyl, said substituted phenylalkynyl, and said substituted phenoxy may be substituted by one or two moieties selected from the group consisting of fluoro, chloro, ($C_1$-$C_3$)alkyl, ($C_1$-$C_3$)-alkoxy and $CF_3$; with the proviso that when $R_1$ and $R_2$ are both hydrogen, $R_6$ cannot be methyl; a pharmaceutically acceptable acid addition salt thereof, or, when $R_6$ is ($C_2$-$C_3$)alkylcarboxy, a pharmaceutically acceptable base addition salt thereof.

Another embodiment of the present invention relates to compounds of the formula I wherein $R_5$ is $R_7$ and Q is $R_1R_2N$— wherein $R_1$ is hydrogen, ($C_1$-$C_{15}$)alkyl, ($C_1$-$C_{15}$)alkyl-($C_3$-$C_8$)cycloalkyl, ($C_2$-$C_{15}$)alkenyl(-$C_3$-$C_8$)cycloalkyl, ($C_2$-$C_{15}$)alkynyl-($C_3$-$C_8$)cycloalkyl, ($C_3$-$C_{15}$)alkynyl, a heteroaryl containing group selected from heteroaryl-($C_1$-$C_{10}$)alkyl, heteroaryl-($C_1$-$C_{10}$)alkenyl, and heteroaryl-$C_1$-$C_{10}$ alkynyl, wherein the heteroaryl moiety is selected from the group consisting of thiophene and furane, ($C_7$-$C_{20}$)-phenylalkenyl, substituted ($C_7$-$C_{20}$)phenylalkenyl, ($C_7$-$C_{20}$)phenylalkynyl, substituted ($C_7$-$C_{20}$)-phenylalkynyl, ($C_1$-$C_6$)alkoxy($C_2$-$C_6$)alkyl, phenoxy-($C_2$-$C_6$)alkyl, substituted phenoxy($C_2$-$C_6$)alkyl, $C_1$-$C_6$)alkoxy-($C_2$-$C_6$)alkenyl, ($C_1$-$C_6$)-alkoxy-($C_2$-$C_6$)alkynyl, phenoxy-($C_2$-$C_6$)alkenyl, substituted phenoxy-($C_2$-$C_6$)alkenyl, phenoxy-($C_2$-$C_6$)-alkynyl, substituted phenoxy-($C_2$-$C_6$)alkynyl, or ($C_7$-$C_{12}$)phenylalkyl-($C_7$-$C_{12}$)phenylalkyl; $R_2$ is hydrogen, ($C_1$-$C_{15}$)alkyl, cyclopentyl, cyclohexyl, ($C_3$-$C_{15}$)alkenyl, phenyl, ($C_7$-$C_{20}$)phenylalkyl which may be substituted in the phenyl by one or two of fluoro, chloro, ($C_1$-$C_3$)alkyl, ($C_1$-$C_3$)alkoxy, or $CF_3$, or ($C_3$-$C_8$)cycloalkyl-($C_1$-$C_{15}$)alkyl; or $R_1$ and $R_2$ together with the nitrogen atom to which they are attached form a pyrrolidinyl or piperidyl which may be substituted by one ($C_1$-$C_6$)alkyl, phenyl, or ($C_7$-$C_{20}$)phenylalkyl; $R_3$ is ($C_1$-$C_6$)alkyl, phenyl, ($C_7$-$C_{20}$)phenylalkyl which may be substituted in the phenyl by one or two fluoro, chloro, ($C_1$-$C_3$)alkyl, ($C_1$-$C_3$)alkoxy, or $CF_3$, or furyl or thienyl which may be substituted by one ($C_1$-$C_3$)-alkyl, ($C_1$-$C_6$)alkyl substituted with carbonyl, chloro, fluoro, bromo, iodo, trifluoromethyl, hydroxy or ($C_1$-$C_3$) alkoxy, ($C_2$-$C_6$)alkenyl, ($C_2$-$C_6$)alkynyl, ($C_3$-$C_6$)cycloalkyl, ($C_1$-$C_{15}$)alkyl-($C_3$-$C_8$)cycloalkyl, ($C_2$-$C_{15}$)alkenyl-($C_3$-$C_8$)cycloalkyl, or ($C_2$-$C_{15}$)alkynyl($C_3$-$C_8$)cycloalkyl; $R_4$ is hydrogen, ($C_1$-$C_6$)alkyl, phenyl or ($C_7$-$C_{20}$)phenylalkyl which may be substituted in the phenyl by one or two of fluoro, chloro, ($C_1$-$C_3$)alkyl, ($C_1$-$C_3$)alkoxy or $CF_3$; and $R_7$ is hydrogen or ($C_1$-$C_6$)alkyl with the provision that when $R_7$ is hydrogen and $R_3$ is ($C_1$-$C_6$)alkyl, then $R_4$ is not hydrogen; and with the provision that when $R_1$ is hydrogen or ($C_1$-$C_{15}$)-alkyl, $R_2$ is not hydrogen, ($C_1$-$C_{15}$)alkyl, cyclopentyl, cyclohexyl, ($C_3$-$C_{15}$)alkenyl, phenyl, or ($C_7$-$C_{20}$)phenylalkyl which may be substituted in the phenyl by one or two of fluoro, chloro, ($C_1$-$C_3$)alkyl, ($C_1$-$C_3$)-alkoxy, or $CF_3$; or $R_1$ and $R_2$ together with the nitrogen atom to which they are attached form a pyrrolidinyl or piperidyl which may be substituted by one ($C_1$–$C_6$)alkyl, phenyl, or ($C_7$–$C_{20}$)-phenylalkyl;

or an acid or, when $R_7$ is hydrogen, a base addition salt thereof.

Another embodiment of the invention relates to compounds of the formula I wherein Q is $SO_nR_{10}$ wherein n is an integer from 0 to 2 and $R_{10}$ is as defined above.

A preferred embodiment of the present invention relates to compounds of formula I wherein $R_1$ and $R_5$ are as defined above, $R_2$ is hydrogen, ($C_7$–$C_{15}$)alkyl, phenyl, substituted phenyl, ($C_7$–$C_{20}$)phenylalkyl, or substituted ($C_7$–$C_{20}$)phenylalkyl, wherein the phenyl moieties on said substituted phenyl and said substituted phenylalkyl may be substituted by one or two moieties selected from the group consisting of chloro and ($C_1$–$C_3$)alkyl; $R_3$ is ($C_1$–$C_6$)alkyl, phenyl which may be substituted by one or two moieties selected from the group consisting of fluoro, chloro, methyl, ethyl, methoxy, ethoxy, and $CF_3$; and $R_4$ is hydrogen, ($C_1$–$C_6$)alkyl, phenyl or phenyl substituted by one or two moieties selected from the group consisting of methyl and ethyl: the pharmaceutically acceptable acid addition salts thereof, and, when $R_5$ is ($C_2$–$C_3$)alkylcarboxy, the pharmaceutically acceptable base addition salts thereof. More preferably, $R_1$ is hydrogen and $R_2$ is other than hydrogen.

Another preferred embodiment of the present invention relates to compounds of the formula I wherein $R^1$ is hydrogen; $R^2$ is ($C_7$–$C_{12}$)phenylalkyl which may be substituted in the phenyl moiety by one or two moieties selected from the group consisting of fluoro, chloro, ($C_1$–$C_3$)alkyl, ($C_1$–$C_3$)alkoxy, and $CF_3$; $R_3$ and $R_4$ are each methyl: and $R_5$ is as defined above pharmaceutically acceptable acid addition salts thereof, and, when $R_5$ is ($C_2$–$C_3$)alkylcarboxy, pharmaceutically acceptable base addition salts thereof.

A particularly preferred embodiment of the present invention relates to compounds of the formula I wherein $R_1$ is hydrogen; $R_2$ is ($C_8$–$C_9$)alkyl, ($C_9$–$C_{12}$)-phenylalkyl, ($C_9$–$C_{12}$)p-chlorophenylalkyl or ($C_{10}$–$C_{13}$)p-methylphenylalkyl; $R_3$ and $R_4$ are each methyl; and $R_5$ is ($C_1$–$C_6$)alkyl or ($C_1$–$C_6$)alkoxy; and the pharmaceutically acceptable acid addition salts thereof.

Specifically preferred compounds of the present invention are as follows:
5-Acetoxy-4,6-dimethyl-2-phenylhexylaminopyrimidine; and 4,6-dimethyl-2-phenylhexylamino-5-(ethyloxyformyl)-oxypyrimidine.

Other specific compounds of the present invention are the title compounds of Examples 2–11 and 13–19 set forth below.

Specific compositions of the invention contain the specific compounds mentioned above and preferred compositions contain the preferred compounds mentioned above.

The invention further includes a method of treating a mammal affected by pulmonary, asthmatic, dermatologic, cardiovascular, allergic or inflammatory diseases with a compound of the formula I as defined above or a pharmaceutically acceptable acid or base addition salt thereof.

The term "alkyl" in the definitions of groups $R_1$, $R_2$, $R_3$, $R_4$, $R_5$ and $R_6$ denotes saturated monovalent straight or branched aliphatic hydrocarbon radicals such as methyl, ethyl, propyl, butyl, t-butyl, hexyl, octyl, 2-ethylhexyl etc.

The term "phenylalkyl" in the definitions of groups $R_2$, $R_3$, $R_4$ and $R_5$ denotes a phenyl group attached to saturated divalent straight or branched aliphatic hydrocarbon radicals. Examples of such phenylalkyls are methylphenyl, ethylphenyl, propylphenyl, butylphenyl, pentylphenyl, hexylphenyl, octylphenyl, 1,1-dimethyl-7-phenylheptyl etc.

DETAILED DESCRIPTION OF THE INVENTION

As shown in Scheme 1, compounds of formula I wherein $R_5$ is $R_7$ and certain compounds of formula I wherein $R_5$ is —$COR_6$ may be prepared by condensing a diketoacyloxy compound of formula II wherein $R_3$ and $R_4$ are as defined above and acyl is any acyl group such as acetyl or benzoyl, with a 1,1-($R_1$,$R_2$)guanidine salt of formula III, wherein $R_1$ and $R_2$ are as previously defined. The condensation is carried out in the presence of an alkaline reagent such as sodium acetate, sodium hydroxide or sodium ethoxide, and an aprotic polar solvent such as dimethylformamide, dimethylsulfoxide or a protic solvent such as aqueous alcohol, at a temperature of 50° to 140° C., usually 100° C., for a time period of about 2 to 24 hours, usually 3 to 5 hours.

The compounds of formula IV formed are treated with a hydride reducing agent to form the corresponding 5-hydroxypyrimidines of formula I. Specific hydride reducing agents are for instance, diisobutylaluminum hydride (Dibal®) and sodium bis(2-methoxyethoxy)-aluminum hydride. The reaction is generally carried out at −78° to 10° C., usually about −23° C., in a dry inert solvent such as tetrahydrofuran, ether, toluene or benzene.

Alternatively, compounds of the formula IV may be hydrolyzed to compounds of the formula I by usual techniques such as reaction with aqueous or alcoholic alkali.

The compounds of formula I wherein $R_1$ is hydrogen and $R_2$ is ($C_7$–$C_{20}$) phenylalkyl may be prepared by reacting a compound of the formula II as defined above with guanidine to form a compound of formula V wherein $R_3$ and $R_4$ are as previously defined. The reaction conditions are as outlined above with respect to condensation of compounds of the formula II with compounds of the formula III.

Scheme 1

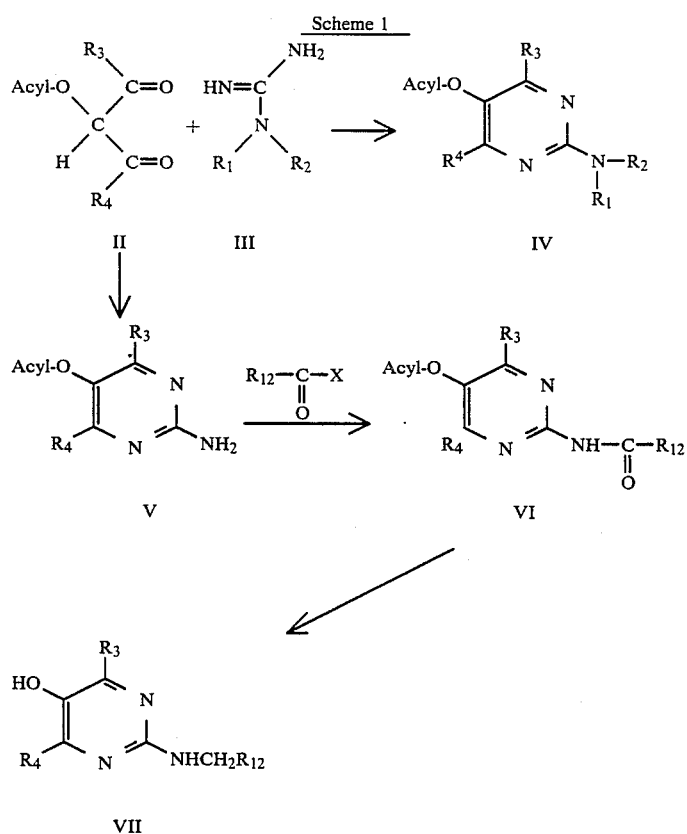

The formed compound of the formula V is then reacted with an acid halide of the formula $R_{12}COX$, wherein X is halogen, preferably chlorine, and $R_{12}$ is $(C_1-C_{14})$alkyl, $(C_2-C_{14})$alkenyl, $(C_3-C_8)$cycloalkyl-$(C_1-C_{14})$alkyl or $(C_6-C_{19})$phenylalkyl which may be substituted in the phenyl group by one to three of fluoro, chloro, $(C_1-C_6)$alkyl, $(C_1-C_6)$alkoxy, or trifluoromethyl. This reaction to form the compound of formula VI is carried out in general at $-20°$ C. to room temperature, usually about 0° C., for at least 15 minutes, for instance about half an hour, depending on the reaction temperature. The reaction may be speeded up by heating the reaction mixture after addition of all of the halide to about 20° to 30° C., e.g. 25° C., for at least about 15 minutes, usually 0.5 hour.

The corresponding compound of formula VII is formed by reacting a compound of formula VI with a hydride reducing agent such as diisobutylaluminum hydride or sodium bis(2-methoxyethoxy)aluminum hydride. The reaction is generally carried out at $-78°$ to $-10°$ C., e.g. at about $-23°$ C., in a dry inert solvent such as tetrahydrofuran, ether, toluene or benzene.

Alternatively, the compound of formula V may be reacted with a compound of the formula $R_1X$ or $R_2X$ wherein $R_1$ and $R_2$ are as defined above and X is mesylate or halogen such as chlorine, bromine or iodine. The reaction conveniently proceeds in the presence of a base such as sodium hydroxide, t-butoxide, sodium hydride or tertiary amines such as triethylamine.

The compounds of formula I wherein $-NR_1R_2$ is an optionally substituted pyrrolidinyl or piperidyl ring may be formed by reaction of the corresponding compound (I) wherein $R_1$ and $R_2$ are hydrogen with a dihalide such as 1,4-dibromobutane or 1,5-dibromopentane or properly substituted derivatives thereof. Alternatively, a compound of the formula I wherein the $NR_1R_2$ group is replaced with methylsulphonyl is reacted with an amine of the formula $R_1R_2NH$ wherein $R_1$ and $R_2$ together with the nitrogen to which they are attached are pyrrolidinyl or piperidinyl which may be substituted by one or two of $(C_1-C_6)$alkyl, phenyl or $(C_7-C_{20})$phenylalkyl which may be substituted in the phenyl by $(C_1-C_6)$alkyl. This method is described in Brown et al., The Pyrimidines, Supplement I, 226 and 227, Wiley-Interscience (1970).

The compounds of formula I wherein $R_7$ is other than hydrogen are formed by reacting the corresponding compound of the formula I wherein $R_5$ is hydrogen with a compound of the formula $R_5X$ wherein X is a group which easily reacts with the hydroxyl group in the compound of the formula I wherein $R_5$ is hydrogen, for instance a halogen such as chlorine, tosyl or mesyl. When $R_7$ is methyl, methylating agents such as dimethylsulfate may be used as well.

The reaction is generally carried out under anhydrous conditions in an aprotic, polar solvent such as tetrahydrofuran, dimethylformamide, or dimethylsulfoxide. Suitable reaction temperatures range from about 0° to about 100° C., usually 25° to 30° C. The reaction is facilitated by forming the phenolate salt of the compounds of the formula I by conducting the reaction in the presence of a base including an organic base such as triethylamine, and an inorganic base such as sodium hydroxide or potassium hydroxide. In that case, the reaction is conducted in an inert atmosphere such as nitrogen to avoid oxidation of the phenolate anion.

The diketo-acyloxy compounds of formula II may be prepared by acylation of a corresponding diketo-halo compound as described by Barillier, D., et al., Bull. Soc. Chim., 1976, 444-448. Thus, 1,3-disubstituted-2-halo-propanedione-1,3 is reacted with a sodium acylate in a solvent such as dimethylsulfoxide. The halogen in the diketo compound is chloro or bromo. The acylate may be any suitable acylate such as an acetate or benzoate.

The diketo-halo compounds may be prepared by halogenation of the corresponding diketones, whereas these diketones may be prepared by known methods such as described by R. Levine et al., J. Am. Chem. Soc., 67, 1510–1512 (1945). Thus, beta-diketones are formed by acylation of ketones with esters by means of sodium amide.

The guanidine salts of formula III used for the preparation of compounds of formula I are commercially available when $R_1$ and $R_2$ are either hydrogen or methyl.

The compounds of the present invention wherein $R_5$ is —$COR_6$ may be prepared by acylating a compound of the formula

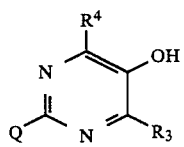

VIII wherein $R_1$, $R_2$, $R_3$ and $R_4$ are as defined for formula I with an acylating agent. Compounds of the formula VIII wherein Q is $R_1R_2N$— are disclosed in European Patent Application Publication No. 0 210 044. Other compounds of the formula VIII wherein Q is $R_1R_2N$— may be prepared as described above. Compounds of the formula VIII wherein Q is $SO_nR_{10}$ may be prepared as described below.

The acylating agent may be an active ester, for example, an anhydride (e.g., acetic anhydride or succinic anhydride) or an acid chloride. Thus for example, the acylating agent may be a compound of the formula

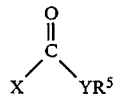

wherein X is chlorine or bromine, Y is oxygen, nitrogen or carbon and $R^5$ is as defined for formula I. Alternatively, the acylating agent may be a compound of the formula

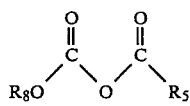

wherein $R^8$ is ($C_1$-$C_6$)alkyl (e.g., isobutyl) and $R_5$ is as defined for formula I, except that $R_5$ cannot be alkoxy or aminoalkyl.

2-Thiopyrimidines may be prepared as described by Chesterfield et al., J. Chem. Soc., 1960, 4595. The thus formed 2-thiopyrimidines are reacted with an alkylating agent such as RX, where X is selected from a group consisting of iodo, chloro, bromo, mesylate and tosylate. The reaction is generally carried out in an aprotic, polar solvent such as tetrahydrofuran or dimethylformamide. Suitable reaction temperatures are from about −23°–100° C., usually 25° C. The reaction is typically carried out under an inert atmosphere such as nitrogen or argon for about 1 to 48 hours, usually about 24 hours. The 5-hydroxy-2-thiopyrimidines may be optionally reacted with an acylating agent as described above for acylating compounds of the formula VIII.

In preparing a compound of the present invention, the acylating agent may be reacted with the hydroxypyrimidine of the formula VII in an inert solvent, such as methylene chloride or ether, in the presence of a base, such as triethylamine or pyridine, under a dry inert atmosphere, such as dry nitrogen or dry argon. Alternatively, a base, such as pyridine, may be used as the solvent. The reaction mixture should preferably be maintained at a temperature of about −20° to about 50° C., more preferably at about 0° C., for about 0.5 to about 24 hours, generally for about 2 hours. After acylation, the product may be treated with an acid, such as phosphoric acid, to form an acid addition salt, or the product may be treated with a base, such as sodium hydroxide, to form a base addition salt.

The acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzensulfonic, and related acids. Preferably, the acid is phosphoric acid.

The base addition salts of the compounds of formula I wherein $R_5$ is ($C_2$-$C_3$)alkylcarboxy may be prepared in a conventional manner by reacting such compounds of the formula I with about one chemical equivalent of an inorganic base such as an alkali metal hydroxide or an alkaline earth metal hydroxide.

The compounds of formula I and their pharmaceutically acceptable acid addition salts are inhibitors of leukotriene synthesis and agents for the treatment of various pulmonary, gastrointestinal, allergic, inflammatory, dermatological and cardiovascular conditions. In particular, the compounds have utility, both as the sole active agent and also in combination with other active agents, for the treatment of mammals, including humans, affected with asthma, bronchitis, pulmonary diseases such as pulmonary hypertension and hypoxia, peptic ulcers, psoriasis, arthritis, inflammatory bowel disease or cardiovascular spasm, such as acute myocardial infarctions.

While we do not wish to be bound by theory, we believe that the acylated derivatives of the present invention are metabolized in vivo to form the corresponding 5-hydroxy compounds.

For treatment of the various conditions described above, the compounds of formula I may be administered to a subject in need of treatment by a variety of conventional routes of administration, including oral, by injection, topical, and in an aerosol carrier composition for administration by breathing or topical application.

In general, a therapeutically-effective dose for the active compounds of formula I will range from 0.01 to 100 mg/kg body weight of the subject to be treated per day, preferably 0.1 to 50 mg/kg per day.

Although the compounds of formula I can be administered alone, they will generally be administered in admixture with a pharmaceutical carrier selected with regard to the intended route of administration and standard pharmaceutical practice. For example, oral administration may be in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water. For parenteral injection, they may be used in the form of a sterile aqueous solution which may contain other solutes, for example enough salt or glucose to make the solution isotonic. For topical use, they may be formulated in solutions, suspensions, gels, creams, or ointments, such formulations preferably including one or more excipients to prevent or retard decomposition, such as ascorbic acid, sodium bisulfite, or dithiothreitol and agents to adjust the pH, such as sodium hydroxide, hydrochloric acid or sodium bicarbonate.

The activity of the compounds of formula I in the treatment of pulmonary (e.g., asthmatic), allergic, dermatological (e.g., psoriasis) and inflammatory diseases may be determined by a standard test measuring an agent's ability to inhibit cyclooxygenase and lypoxygenase enzyme activity of rat basophil leukemia (RBL-1) cells. According to this test as described by Jakschick et al., *Prostaglandins*, 16,733–747 (1978), a monolayer of RBL-1 cells is grown for 1 or 2 days in spinner culture in Eagle's minimum essential medium, 15% heat-inactivated fetal calf serum and an antibiotic/antimycotic mixture. The cells are washed after centrifugation and incubated in a buffer. A volume of 0.5 ml of cell suspension is preincubated at 30° C. for ten minutes with a 1 microliter dimethylsulfoxide (DMSO) solution of the agent to be tested. The incubation is initiated by simultaneous addition of 5 microliters of ($^{14}$C)- arachidonic acid in ethanol and 2 microliters of calcium ionophore (A-21387) in DMSO for final concentrations of 5 and 7.6M, respectively. Five minutes later, the incubation is terminated by the addition of 0.27 ml acetonitrile/acetic acid (100:3). Thin layer chromatography is performed using acetonitrile/water/acetic acid solvent.

The following Examples illustrate the invention. All melting points referred to in the Examples are uncorrected.

EXAMPLE 1

5-Acetoxy-4,6-dimethyl-2-phenylhexylaminopyridimidine 4,6-Dimethyl-5-hydroxy-2-phenylhexylaminopyrimidine (0.53 g. 1.77 mmol) was dissolved in dry methylene chloride (10 ml) and treated sequentially with triethyl amine (0.25 ml) and acetic anhydride (0.18 g 1.77 mmol) while chilling to 0° C., under a nitrogen atmosphere. After being stirred for 18 hours, the reaction mixture was concentrated on a rotary evaporator. The residue was dissolved in ethyl acetate (50 ml) and extracted three times with water (75 ml) and one time with brine (50 ml). The dried organic extracts were filtered and concentrated on a rotary evaporator and chromatographed on silica gel, eluted with 1:3, ethyl acetate:hexanes to afford 0.45 g of product, mp: 63°–65° C. Mass spectrum m/e=341. NMR (CDCl$_3$) delta: 7.01 (bs, 5H); 5.03–4.78 (m, 1H); 3.41–3.15 (m, 2H); 2.70–2.41 (M, 2H); 2.2 (s 3H); 2.09 (s, 6H); 1.71–1.43 (m, 10H). IR (CHCl$_3$): 3445, 1763, 1763, 1583, 1517 cm$^{-1}$.

EXAMPLE 2

5-Benzoyloxy-4,6-dimethyl-2-phenylhexylaminopyrimidine 4,6-Dimethyl-5-hydroxy-2-phenylhexylaminopyrimidine (0.5 g, 1.7 mmol) was dissolved in pyridine (20 ml), cooled to 0° C. under nitrogen and treated with benzoyl chloride (0.2 ml, 1.7 mmol). After being stirred for 2 hours the reaction mixture was poured into water (100 ml) and extracted with ethyl acetate (3×25 ml). The combined organics were dried and concentrated and the residue chromatographed to afford 0.41 g of product, mp: 79°–80° C. Mass spectrum m/e= 403. NMR (CHCl$_3$) delta: 8.23 (d, 5 Hz, 2H); 7.62–7.10 (m, 8H); 5.04–4.98 (m, 1H); 3.36 (q, 7, 3 Hz, 2H); 2.56 (t, 5 Hz, 2H); 2.18 (s, 6H); 1.68–1.30 (m, 8H). IR (KBr): 1740, 1600, 1580, 1550 cm$^{-1}$. Anal Calc'd for C$_{25}$H$_{29}$N$_3$O$_2$: C, 74.41; H, 7.24; N, 10.41. Found: C, 74.46; H, 7.04; N, 10.17.

EXAMPLE 3

4,6-Dimethyl-2-phenylhexylamino-5-o-toluyloxypyrimidine

In a manner similar to that of the method of Example 2, the title compound was prepared from 0.75 g (2.5 mmol) of 4,6-dimethyl-2-phenylhexylamino-5-hydroxypyrimidine to afford 0.25 g of product, mp: 52°–53° C. Mass spectrum m/e=417. NMR (CDCl$_3$) delta: 8.15 (d, 4 Hz, 1H); 7.46–7.10 (m, 8H); 4.98 (bs, 1H); 3.37 (q, 5, 3 Hz, 2H) 2.66 (s, 3H); 2.60 (t, 4 Hz, 2H), 2.23 (s, 6H); 1.68–1.30 ( m, 8H). IR (CHCl$_3$): 1740, 1580 cm$^{-1}$. Anal. Calc'd for C$_{26}$H$_{31}$N$_3$O$_2$: C, 74.79; H, 7.48; N, 10.06. Found: C, 74.65; H, 7.55; N, 10.10.

EXAMPLE 4

5-Caproyloxy-4,6-dimethyl-2-phenylhexylaminopyrimidine

In a manner similar to that of the method of Example 2, the title compound was prepared from 0.75 g (2.5 mmol) of 4,6-dimethyl-5-hydroxy-2-phenylhexylaminopyrimidine to afford 0.71 g of product, mp: 44°–45° C. Mass spectrum m/e=383. NMR (CDCl$_3$) delta: 7.26–7.10 (m, 5H): 5.03 (bs, 1H); 3.32 (q, 5, 3 Hz, 2 H); 2.62–2.48 ( m, 4H); 2.14 (s, 6H): 1.78–0.88 (m, 15 H). IR (CHCl$_3$). 1750, 1600, 1580 cm$^{-1}$. Anal. Calc'd for C$_{23}$H$_{33}$N$_3$O$_2$: C, 72.03; H, 8.67; N, 10.96. Found: C, 71.85; H, 8.65; N, 10.69.

EXAMPLE 5

4,6-Dimethyl-5-(oxo-(1-carboxy-5-phenylpentane))-2-phenylhexylaminopyrimidine

In a manner similar to that of the method of Example 2, the title compound was prepared from 0.75 g (2.5 mmol) of 4,6-dimethyl-5-hydroxy-2-phenylhexylaminopyrimidine to afford 0.8 g of product, mp: 72°–73° C. Mass spectrum m/e=459. NMR (CDCl$_3$) delta: 7.28–7.06 (m, 10H); 4.88 (bs, 1H); 3.32 (q, 5, 3 Hz, 2H): 2.68–2.50 ( m, 6H): 2.12 (s, 6H): 1.84–1.28 (m, 12H). IR (KBr): 1750, 1600 1580 cm$^{-1}$. Anal. Calc'd for C$_{29}$H$_{37}$N$_3$O$_2$: C, 75.78: H, 8.11; N, 9.14. Found: C, 75.46; H, 7.87; N, 8.99.

EXAMPLE 6

4,6-Dimethyl-5-[p-N,N-diethylmethylamino)]-benzoyloxy-2-phenylhexylaminopyrimidine In a manner similar to that of the method of Example 1, the title compound was prepared from 0.75 g (2.5 mmol) of 4,6-dimethyl-5-hydroxy-2-phenylhexylaminopyrimidine to afford 0.62 g of product, mp: 49°–51° C. Mass spectrum m/e =488. NMR (CDCl$_3$) delta 8.10 (d, 4 Hz, 2H): 7.47 (d, 4 Hz, 2H): 7.30–7.06 (m, 5H); 4.92 (bs, 1H); 3.62 (s, 2H); 3.35 (m, 2H); 2.64–2.44 (m, 6H); 2.20 (s, 6H); 1.70–1.28 (m, 8H); 1.04 (t, 3 Hz, 6H). IR (CHCl$_3$). 1740, 1580 cm$^{-1}$. Anal. Calc'd for C$_{30}$H$_{40}$N$_4$O$_2$: C, 73.74; H, 8.25; N, 11.47. Found: C, 73.40; H, 8.25; N, 11.25.

EXAMPLE 7

4,6-Dimethyl-2-phenylhexylamino-5-succinoyloxypyrimidine

In a manner similar to that of the method of Example 1, the title compound was prepared from 0.75 g (2.5 mmol) of 4,6-dimethyl-5-hydroxy-2-phenylhexylaminopyrimidine and succinic anhydride (0.25 g, 2.5 mmol) to afford 0.45 g of product, mp: 171°–172° C. Mass spectrum m/e=399. NMR (DMSO-d$_6$) delta: 7.24–6.90 (m, 6H); 3.21–3.09 (m, 2H); 2.80–2.48 (m, 6H); 2.04 (s, 6H); 1.58–1.22 (m, 8H). IR (KBr): 1700, 1595 cm$^{-1}$. Anal. Calc'd for C$_{22}$H$_{29}$O$_4$N$_3$: C, 66.15; H, 7.32; N, 10.52. Found: C, 65.75; H, 7.24; N, 10.41.

EXAMPLE 8

4,6-Dimethyl-5-[(p-morpholinomethyl)]-benzoyloxy-2-phenylhexylaminopyrimidine In a manner similar to that of the method of Example 1, the title compound was prepared from 0.78 g (2.33 mmol) of 4,6-dimethyl-5-hydroxy-2-phenylhexylaminopyrimidine and p-morpholinomethylbenzoyl chloride (2.8 mmol) to afford 0.43 g of product, mp: 81°–84° C. Mass spectrum m/e=502. NMR (CDCl$_3$) delta: 8.00 (d, 4 Hz, 2H); 7.35 (d, 4 Hz, 2H); 7.20–7.00 (m, 5H); 4.9 (m, 1H); 3.70–3.30 (m, 8H): 2.58–2.30 (m, 4H); 2.16 (s, 6H); 1.64–1.28 (m, 8H). IR (CHCl$_3$): 1739, 1582 cm$^{-1}$. Anal. Calc'd for C$_{30}$H$_{38}$N$_4$O$_3$: C, 71.68; H, 7.62; N, 11.15. Found: C, 71.83; H, 7.70; N,10.98.

EXAMPLE 9

4,6-Dimethyl-2-phenylhexylamino-5-propanoyloxypyrimidine

In a manner similar to that of the method of Example 2, the title compound was prepared from 0.94 g (3.12 mmol) of 4,6-dimethyl-5-hydroxy-2-phenylhexylaminopyrimidine to afford 0.76 g of product, mp: 66°–67° C. Mass spectrum m/e=355. NMR (CDCl$_3$) delta: 7.21–7.01 (m, 5H); 4.95 (bs, 1H); 3.34–3.21 (m, 2H); 2.61–2.42 (m, 4 R); 2.12 (s, 6H); 1.64–1.21 (m, 11H). IR (CHCl$_3$) 1756, 1579 cm$^{-1}$. Anal. Calc'd for C$_{21}$H$_{29}$N$_3$O$_2$: C, 70.75; H, 8.22; N, 11.82. Found: C, 70.99; H, 7.92; N, 11.91.

EXAMPLE 10

4,6-Dimethyl-2-phenylamino-5-(2-thienoyl)oxypyrimidine

In a manner similar to that of the method of Example 2, the title compound was prepared from 0.88 g (2.95 mmol) of 4,6-dimethyl-5-hydroxy-2-phenylhexylaminopyrimidine to afford 0.83 g of product, mp: 91°–93° C. Mass spectrum m/e=409. NMR (CDCl$_3$) delta: 7.91 (d, 2 Hz, 1H); 7.62 (d, 2 Hz, 1H); 7.24–7.10 (m, 6H); 4.97 (bs, 1H); 3.32 (q, 7, 5 Hz, 2H); 2.57 (t, 4 Hz, 2H); 2.19 (s, 6H); 1.64–1.30 (m, 8H). IR (CHCl$_3$): 1729, 1580 cm$^{-1}$. Anal. Calc'd for C$_{23}$H$_{27}$N$_3$O$_2$S: C, 67.45; H, 6.65; N, 10.26. Found: C, 67.62; H, 6.76; N, 10.10.

EXAMPLE 11

4,6-Dimethyl-2-phenylhexylamino-5-(phenyloxyformyl)oxypyrimidine

In a manner similar to that of the method of Example 2, the title compound was prepared from 0.76 g (2.6 mmol) of 4,6-dimethyl-5-hydroxy-2-phenylhexylaminopyrimidine and phenyl chloroformate (0.40 g, 2.6 mmol) to afford 0.74 g of product, mp: 76°–77° C. Mass spectrum m/e=419. NMR (CDCl$_3$) delta: 7.4–6.9 (m, 10H); 4.99 (bs, 1H); 3.3 (q, 7, 4 Hz, 2H); 2.5 (t, 4 Hz, 2H); 2.3 (s, 6H); 1.8–1.1 (m, 8H). IR (CHCl$_3$): 1780, 1583 cm$^{-1}$. Anal. Calc'd for C$_{25}$H$_{29}$N$_3$O$_3$: C, 71.57; H, 6.97: N, 10.02. Found: C, 71.51; H, 6.95; N, 10.09.

EXAMPLE 12

4,6-Dimethyl-2-phenylhexylamino-5-(ethyloxyformyl)oxypyrimidine

A. In a manner similar to that of Example 1, the title compound was prepared from 4.71 g (12 mmol) of 4,6-dimethyl-5-hydroxy-2-phenylhexylaminopyrimidine phosphate salt, triethylamine (16.52 ml, 120 mmol) and ethyl chloroformate (1.7 ml, 18 mmol) to afford 3.8 g of product, mp: 44°–45° C. Mass spectrum m/e=371. NMR (CDCl$_3$) delta: 7.34–7.16 (m, 5H): 5.00 (bs, 1H); 4.36 (q, 6, 3 Hz, 2H): 3.40 (q, 6, 3 Hz, 2H): 2.65, (t, 3 Hz, 2H); 1.74–1.36) (m, 11H). IR (CHCl$_3$): 1761, 1583 cm$^{-1}$. Anal. Calc'd for C$_{21}$H$_{29}$N$_3$O$_3$: C, 67.90 H, 7.87; N, 11.31. Found: C, 67.95; H, 7.85; N, 11.14.

B. The title compound (0.1 g, 0.27 mmol) was dissolved in isopropanol (5 ml), cooled to 0° C. and treated with phosphoric acid (0.031 g, 0.27 mmol). After being stirred for 1 hour, the reaction mixture was allowed to come to 25° C., the solvent was removed on a rotary evaporator and the product was recrystallized from ethyl acetate to provide the phosphoric acid addition salt of the title compound, mp: 105°–107° C. Anal. Calc'd for C$_{21}$H$_{29}$O$_3$H$_3$H$_3$PO$_4$: H : C, 53.73: H, 6.87; N, 8.95. Found: C, 53.66; H, 6.84; N, 8.80.

EXAMPLE 13

4,6-Dimethyl-2-phenylhexylamino-5-(isobutyloxyformyl)oxypyrimidine

In a manner similar to that of the method of Example 2, the title compound was prepared from 0.7 g (2.3 mmol) of 4,6-dimethyl-5-hydroxy-2-phenylhexylaminopymidine and isobutyl chloroformate (0.31 ml, 2.3 mmol) to afford 0.79 g of product. Mass spectrum m/e=399. NMR (CDCl$_3$) delta: 7.28–7.10 (m, 5H); 4.86 (bs, 1H): 4.05 (d, 4 Hz, 2H): 3.39 (q, 4, 6 Hz, 2H); 2.58 (t, 5 Hz, 2H): 2.22 (s, 6H): 2.10–1.96 (m, 1H): 1.70–1.30 (m, 8H); 0.99 (d, 4 Hz, 6H). IR (CHCl$_3$) 1760, 1580 cm$^{-1}$. Anal. Calc'd for C$_{23}$H$_{33}$O$_3$N$_3$: C, 69.14: H, 8.32: N, 10.52. Found: C, 69.20; H, 8.12; N, 10.89.

EXAMPLE 14

5-(N,N-Dimethylaminoformyl)oxy-4,6-dimethyl-2-phenylhexylaminopyrimidine

In a manner similar to that of the method of Example 2, the title compound was prepared from 0.5 g. (1.7 mmol) of 4,6-dimethyl-5-hydroxy-2-phenylhexylaminopyrimidine and N,N-dimethylcarbamoyl chloride (0.15 ml, 1.7 mmol) to afford 0.55 g of product, mp: 81°-82° C. Mass spectrum m/e=370. NMR (CDCl$_3$) delta: 7.30-7.10 (m, 5H); 4.88 (bs, 1H): 3.34 (q, 4, 6 Hz, 2 H); 3.11 (s, 3H); 3.00 (s, 3H): 2.58 (t, 5 Hz, 2H): 2.20 (s, 6H): 1.68-1.32 (m, 8H). IR (CHCl$_3$) 1730, 1590 cm$^{-1}$. Anal. Calc'd for $C_{21}H_{30}O_2N_4$: C, 68.08; H, 8.16; N, 15.12. Found: C, 68.08; H, 7.99; N, 14.75.

EXAMPLE 15

5-(N,N-Dimethylaminoformyl)oxy-4-isopropyl-6-methyl-2-phenylhexylaminopyrimidine In a manner similar to that of the method of Example 2, the title compound was prepared from 0.45 g (1.4 mmol) of 5-hydroxy-4-isopropyl-6-methyl-2-phenyl hexylaminopyrimidine and N,N-dimethylcarbamoyl chloride (0.13 ml, 1.4 mmol) to afford 0.4 g of product, mp: 41°-42° C. Mass spectrum m/e=398. NMR (CDCL$_3$) delta: 7.25-7.04 (m, 5H): 4.83 (bs, 1H): 3.33 (q, 5, 3 Hz, 2H); 3.10 (s, 3H); 3.00 (s, 3H); 2.85-2.97 (m, 1H); 2.57 (t, 4 Hz, 2H): 2.16 (s, 3H): 1.68-1.30 (m, 8H); 1 15 (d, 4 Hz, 6H). IR (CHCl$_3$) 1725, 1580 cm$^{-1}$. Anal. Calc'd for $C_{23}H_{34}O_2N_4$: C, 69.32: H, 8.60: N, 14.06. Found: C, 69.43: H, 8.50: N, 13.75.

EXAMPLE 16

4,6-Dimethyl-5-oxo(1-carboxy-2,2-dimethylpropane)-2-phenylpentylaminopyrimidine

In a manner similar to that of the method of Example 2, the title compound was prepared from 0.5 g (1.8 mmol) of 4,6-dimethyl-5-hydroxy-2-phenylpentylaminopyrimidine and pivaloyl chloride (0.22 ml, 1.8 mmol) to afford 0.33 g of product, mp: 79°-80° C. Mass spectrum m/e=369. NMR (CDCl$_3$) delta: 7.32-7.14 (m, 5H): 5.48 (bs, 1H): 3.36 (q, 5, 3 Hz, 2H): 2.61 (t, 4 Hz, 2H): 2.15 (s, 6H): 1.67-1.42 (m, 6H); 1.40 (s, 9H). IR (CHCl$_3$): 1750, 1580 cm$^{-1}$. Anal. Calc'd for $C_{22}H_{31}O_2N_3$: C, 71.51: H, 8.46: N, 11.37 Found: C, 71.06; H, 8.31: N, 10.94.

EXAMPLE 17

4,6-Dimethyl-2-phenylpentylamino-5-(isobutyloxyformyl)oxypyrimidine

In a manner similar to that of the method of Example 2, the title compound was prepared from 0.5 g (1.8 mmol) of 4,6-dimethyl-5-hydroxy-2-phenylpentylaminopyrimidine and isobutylchoroformate (0.23 ml, 1.8 mmol) to afford 0.45 g of product. Mass spectrum m/e=385. NMR (CDCl$_3$) delta: 7.27-7.16 (m, 5H): 5.00 (bs, 1H); 4.06 (d, 5 Hz, 2H); 3.00-3.60 (m, 2H); 2.61 (t, 4 Hz, 2H); 2.23 (s, 6H): 1.65-1.36 (m, 6H): 0.99 (d, 4 Hz, 6H). IR (CHCl$_3$) 1760, 1580 cm$^{-1}$. Anal. Calc'd for $C_{22}H_{31}O_3N_3$: C, 68.54: H, 8.10: N, 10.90. Found: C, 68.14; H, 7.85; N, 10.69.

EXAMPLE 18

5-Benzoyloxy-4,6-dimethyl-2-phenylhexylaminopyrimidine

In a manner similar to that of the method of Example 2, the title compound was prepared from 0.5 g (1.8 mmol) of 4,6-dimethyl-5-hydroxy-2-phenylpentylaminopyrmidine and benzoyl chloride (0.2 ml, 1.8 mmol) to afford 0.43 g of product, mp: 51°-53° C. Mass spectrum m/e=389. NMR (CDCl$_3$) delta 8.22 (d, 5 Hz, 2H); 7.66 (t, 2 Hz, 1H): 7.53 (t, 2 Hz, 2H); 7.30-7.19 (m, 5 H); 5.09 (bs, 1H); 3.39 (q, 7, 3 Hz, 2H); 2.61 (t, 5 Hz, 2H); 2.22 (s, 6H): 1.70-1.38 (m, 6H). IR (CHCl$_3$): 1735, 1570 cm$^{-1}$. Anal. Calc'd for $C_{24}H_{27}O_2N_3$: C, 74.01; H, 6.99: N, 10.79. Found: C, 74.52; H, 7.04; N, 10.73.

EXAMPLE 19

5-(N,N-Dimethylaminoformyl)oxy-4,6-dimethyl-2-phenylpentylaminopyrimidine

In a manner similar to that of the method of Example 2, the title compound was prepared from 1.0 g (3.6 mmol) of 4,6-dimethyl-5-hydroxy-2-phenylpentylaminopyrmidine and N,N-dimethylaminocarbamoyl chloride (0.32 ml, 3.6 mmol) to afford 0.55 g of product, mp: 63°-64° C. Mass spectrum m/e=356. IR (CHCl$_3$) 1720: 1720, 1580 cm$^{-1}$. Anal. Calc'd for $C_{20}H_{28}O_2N_4$: C, 67.39; H, 7.92: N, 15.72. Found: C, 66.95; H, 7.92; N, 15.52.

EXAMPLE 20

4,6-Dimethyl-5-hydroxy-2-(n-heptyl)thiopyrimidine 4,6-Dimethyl-5-hydroxy-2-thiopyrimidine hydrochloride (J. Chem. Soc., 4595, (1960)) (6.84 g, 36 mmol) was stirred in dimethylformamide (100 ml) and treated successively with sodium bicarbonate (3.0 g, 36 mmol) and iodoheptane (8.05 g, 5.83 mL, 36 mmol). After being stirred at 25° C. under nitrogen for 2 hours, the reaction mixture was warmed to 60° C. for 2.5 hours. The reaction mixture was allowed to cool, and stirring was continued for 48 hours. The reaction mixture was concentrated, diluted with ether (100 ml) and the organics were washed five times with water (250 ml), dried and concentrated. The residue was recrystallized from ether to afford 2.3 g (25%) of the title compound, m.p.: 110°-111° C. Anal. Calc'd for $C_{13}H_{22}N_2OS$: C, 61.38; H, 8.71; N, 11.01. Found: C, 60.99: H, 8.50; N, 11.12.

EXAMPLE 21

4,6-Dimethyl-5-hydroxy-2-(n-nonyl)thiopyrimidine

In a manner similar to that of the method of Example 20, the title compound was prepared from 4,6-dimethyl-5-hydroxy-2-thiopyrimidine hydrochloride (5.75 g, 22.6 mmol) and iodononane (6.07 g, 22.6 mmol) to provide 1 g of product (15%), m.p.: 79°-81° C. Anal. Calc'd for $C_{16}H_{28}N_2OS$: C, 64.82; H, 9.52; N, 9.45. Found: C, 62.82; H, 9.27: N, 9.38. M. S. 297 (p+1).

EXAMPLE 22

4,6-Dimethyl-5-hydroxy-2-(p-chlorobenzyl)thiopyrimidine

In a manner similar to that of the method of Example 20, the title compound was prepared from 4,6-dimethyl-5-hydroxy-2-thiopyrimidine hydrochloride (2.0 g, 10 mmol) and p-chlorobenzyl chloride (1.7 g, 10 mmol) to yield 1.5 g of product (52%), m.p.: 182°-183° C. Anal. Calc'd for $C_{13}H_{13}N_2OSCl$: C, 55.61; H, 4.67; N, 9.98. Found: C, 56.06; H, 4.76; N, 10.18. M.S. 280 (p).

EXAMPLE 23

4,6-Dimethyl-5-hydroxy-2-(p-methylbenzyl)thiopyrimidine

In a manner similar to that of the method of Example 20, the title compound was prepared from 4,6-dimethyl-5-hydroxy-2-thiopyrimidine hydrochloride (2.0 g, 10 mmol) and p-methylbenzyl chloride (1.5 g, 10 mmol) to yield 0.6 g of product (22%), m.p.: 206°-207° C. Anal.

Calc'd for $C_{14}H_{16}N_2OS$: C, 64.59; H, 6.19; N, 10.76. Found: C, 64.83: H, 6.16; N, 10.89 M. S. 260 (p).

EXAMPLE 24

4,6-Dimethyl-5-hydroxy-2-(5-phenyl-1-pentyl)thiopyrimidine

In a manner similar to that of the method of Example 20, the title compound was prepared from 4,6-Dimethyl-5-hydroxy-2-thiopyrimidine hydrochloride (1.0 g, 5.2 mmol) and 5-phenyl-1-n-pentyl tosylate (1.7 g, 5.2 mmol) to yield 0.11 g of product (7%), m.p.: 58°-60° C. Anal. Calc'd for $C_{17}H_{22}N_2OS$: C, 67.51; H, 7.33; N, 9.26. Found: C, 67.80: H, 7.33; N, 8.64. M. S. 302 (p).

EXAMPLE 25

4,6-Dimethyl-5-hydroxy-2-benzylthiopyrimidine

In a manner similar to that of the method of Example 20, the title compound was prepared from 4,6-Dimethyl-5-hydroxy-2-thiopyrimidine hydrochloride (1.5 g, 7.8 mmol) and benzyl bromide (1.3 g, 7.8 mmol) to yield 0.6 g of product (31%), m.p.: 222°-223° C. Anal. Calc'd for $C_{13}H_{14}N_2OS$: C, 63.39: H, 5.73; N, 11.37. Found: C, 63.53: H, 5.79: N, 11.44. M. S. 246 (p).

EXAMPLE 26

The title compound of Example 1, 16 and 17 were treated by the method of Jakschick et al., *Prostaglandins*, 16, 733-747 (1978), for their ability to inhibit lipoxygenase enzyme activity. All compounds were effective at a level of 10 micromolar.

EXAMPLE 27

4,6-Dimethyl-5-((1-oxycarboxyethyl)ethoxy)-2-phenylhexyl aminopyrimidine 5.0 g (16.7 mmol) 4,6-dimethyl-5-hydroxy-2-phenylhexylaminopyrimidine 7.64 g (16.7 mmol) chloroethylethylcarbonate, 3.54 g (33.4 mmol) sodium carbonate and 12.52 g (83.5 mmol) sodium iodide were combined in a round bottom flask and stirred at 25° C. for 72 hours under nitrogen. The reaction was concentrated on a rotovap, dissolved in ethyl acetate (125 ml) and extracted with water (50 ml) and brine (50 ml). The extracts were dried, filtered, concentrated on a rotovap and purified by chromatography to provide 0.23 g of product. Mass spectrum m/e=415. NMR (CDCl$_3$) 7.3-7.1 (m, 4 H): 5.9 (q, 6, 3 Hz, 1 H): 4.80 (bs, 1 H): 4.06 (q, 7, 4 Hz, 2 H): 3.38-3.26 (m, 2 H): 2.58 (t, 5 Hz, 2 H): 2.30 (s, 6 H): 1.70-1.18 (m, 14 H). IR (CHCl$_3$) 1745, 1571 cm$^{-1}$. Anal. Calc'd for $C_{22}H_{33}N_3O_3$: C, 66.48: H, 8.01: N, 10.11. Found: C, 66.47; H, 7.80: N, 10.27.

We claim:
1. A compound of the formula

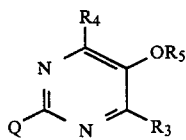

wherein Q is $R_1R_2N$— or $SO_nR_{10}$, wherein n is an integer from 0 to 2, $R_1$ is hydrogen, $(C_1-C_{15})$alkyl, $(C_1-C_{15})$alkyl -$(C_3-C_8)$-cycloalkyl, $(C_2-C_{15})$alkenyl - $(C_3-C_8)$cycloalkyl, $(C_2-C_{15})$alkynyl - $(C_3-C_8)$cycloalkyl, $(C_3-C_{15})$alkynyl, a heteroaryl containing group selected from heteroaryl - $(C_1-C_{10})$alkyl, heteroaryl -$(C_1-C_{10})$ alkenyl, and heteroaryl -$(C_1-C_{10})$alkynyl, wherein the heteroaryl moiety is selected from the group consisting of thiophene and furane, $(C_7-C_{20})$phenylalkenyl, substituted $(C_7 C_{20})$phenylalkenyl, $(C_7-C_{20})$phenylalkynyl, substituted $(C_7-C_{20})$phenylalkynyl, $(C_1-C_6$ alkoxy) - $(C_2-C_6)$alkyl, phenoxy -$(C_2-C_6)$alkyl, substituted phenoxy -$(C_2-C_6)$alkyl, $(C_1-C_6)$alkoxy$(C_2-C_6)$alkenyl, $(C_1-C_6)$alkoxy -$(C_2-C_6)$alkynyl, phenoxy -$(C_2-C_6)$alkenyl, substituted phenoxy- $(C_2-C_6)$alkenyl, phenoxy -$(C_2-C_6)$alkynyl, substituted phenoxy- $(C_2-C_6)$alkynyl, or $(C_7-C_{12}$- phenylalkyl- $(C_7-C_{12})$phenylalkyl; $R_2$ is hydrogen, $(C_1-C_{15})$alkyl, cyclopentyl, cyclohexyl, $(C_3-C_{15})$alkenyl, phenyl, substituted phenyl, $(C_7-C_{20})$phenylalkyl, substituted $(C_7-C_{20})$phenylalkyl or $(C_3-C_8)$cycloalkyl -$(C_1-C_{15})$alkyl; or $R_1$ and $R_2$ together with the nitrogen atom to which they are attached form a pyrrolidinyl or piperidyl group which may be substituted by one $(C_1-C_6)$alkyl, phenyl or $(C_7-C_{20})$phenylalkyl; $R_3$ and $R_4$ are independently selected from the group consisting of hydrogen, $(C_1-C_6)$alkyl, phenyl, substituted phenyl, $(C_1-C_{20})$phenylalkyl, substituted $(C_7C_{20})$phenylalkyl, furyl, thienyl, furyl substituted by one $(C_1-C_3)$alkylo, thienyl substituted by one $(C_1-C_3)$alkyl, $(C_1-C_6)$alkyl substituted with carbonyl, chloro, fluoro, bromo, iodo, trifluoromethyl, hydroxy or alkoxy $(C_1-C_3)$, $(C_2-C_6)$alkenyl, $(C_2-C_6)$alkynyl, $(C_3-C_6)$cycloalkyl, $(C_1-C_{15})$alkyl -$(C_3-C_8)$cycloalkyl, $(C_2-C_{15})$alkenyl-$(C_3-C_8)$cycloalkyl; or $(C_2-C_{15})$alkynyl-$(C_3-C_8)$cycloalkyl; $R_5$ is —COR$_6$, —CH(CH$_3$)OCOOR$_{11}$, or —CH$_2$OCOOR$_{11}$; $R_6$ is hydrogen, $(C_1-C_{10})$ alkyl, $(C_1-C_{10})$alkoxy, phenyl, substituted phenyl, $(C_7-C_{20})$phenylalkyl, substituted $(C_7-C_{20})$-phenylalkyl, $(C_2-C_3)$alkylcarboxy, —NR$_8$R$_9$, wherein R$_8$ and R$_9$ are independently selected from the group consisting of $(C_1-C_{10})$-alkyl, phenyl, substituted phenyl, $(C_7-C_{20})$phenylalkyl and substituted $(C_7-C_{20})$-phenylalkyl; R$_{10}$ is $(C_5-C_{15})$alkyl, $(C_5-C_{15})$alkenyl, phenyl, substituted phenyl, $(C_7-C_{20})$phenylalkyl, substituted $(C_7-C_{20})$phenylalkyl, $(C_7-C_{20})$phenylalkyl-$(C_7-C_{20})$-phenylalkyl- $(C_7-C_{20})$-phenylalkyl, $(C_1-C_{17})$alkyl- $(C_3-C_8)$cycloalkyl, $(C_2-C_{17})$alkenyl- $(C_3-C_8)$cycloalkyl, $(C_2-C_{17})$alkynyl- $(C_3-C_8)$cycloalkyl, $C_5-C_{15}$- alkynyl, a heteroaryl containing group selected from heteroaryl($C_1-C_{10})$alkyl, heteroaryl-$(C_1-C_{10})$alkenyl, and heteroaryl- $(C_1-C_{10})$alkynyl, wherein the heteroaryl moiety is selected from the group consisting of thiophene, and furane, $(C_7-C_{20})$-phenylalkenyl, substituted $(C_7-C_{20})$phenylalkenyl, $(C_7-C_{20})$phenylalkynyl, substituted $(C_7-C_{20})$-phenylalkynyl, $(C_1-C_6)$alkoxy- $(C_4-C_6)$alkyl, phenoxy-$(C_2-C_6)$alkyl, substituted phenoxy- $(C_2-C_6)$alkyl, $(C_3-C_6)$alkyl, $(C_1-C_6)$alkoxy- $(C_3-C_6)$alkenyl, $(C_1-C_6)$alkenyl, $(C_1-C_6)$alkoxy- $(C_3-C_6)$alkynyl, phenoxy- $(C_3-C_6)$alkenyl, substituted phenoxy- $(C_3-C_6)$alkenyl, phenoxy- $C_3-C_6$(alkynyl), or substituted phenoxy- $(C_3-C_6)$alkynyl; wherein the phenyl moieties on said substituted phenyl, said substituted phenylalkyl, said substituted phenylalkenyl, said substituted phenylalkynyl, and said substituted phenoxy may be substituted by one or two moieties selected from the group consisting of fluoro, chloro, bromo, iodo, hydroxy, $(C_1-C_3)$alkyl, $(C_1-C_3)$alkoxy and CF$_3$; R$_{11}$ is $(C_1-C_4)$alkyl; with the proviso that when R$_1$ and R$_2$ are both hydrogen, R$_6$ cannot be methyl; and with the proviso that when Q is $R_1R_2N$— and R$_1$ is hydrogen or $(C_1-C_{15})$alkyl, R$_2$ is not hydrogen, $(C_1-C_{15})$alkyl, cyclopentyl, cyclohexyl, $(C_3-C_{15})$- alkenyl, phenyl, or $(C_7-C_{20})$phenylalkyl which may be substituted in the phenyl by one or two of fluoro, chloro, $(C_1-C_3)$alkyl, $(C_1-C_3)$alkoxy, or CF$_3$;

and with the proviso that when Q is $R_1R_2N-$, $R_3$ and $R_4$ are not both hydrogen; or a pharmaceutically acceptable acid addition salt thereof, or, when $R_6$ is $(C_2-C_3)$alkylcarboxy, a pharmaceutically acceptable base addition salt thereof.

2. A compound according to claim 1, said compound being a compound of the formula

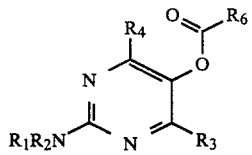

IA wherein $R_1$ is hydrogen, $(C_1-C_{15})$alkyl, $(C_1-C_{15})$-alkyl-$(C_3-C_8)$cycloalkyl, $(C_2-C_{15})$alkenyl-$(C_3-C_8)$-cycloalkyl, $(C_2-C_{15})$alkynyl-$(C_3-C_8)$cycloalkyl, $(C_3-C_{15})$alkynyl, a heteroaryl containing group selected from heteroaryl-$(C_1-C_{10})$alkyl, heteroaryl-$(C_1-C_{10})$-alkenyl, and heteroaryl-$(C_1-C_{10})$-alkynyl, wherein the heteroaryl moiety is selected from the group consisting of thiophene and furane, $(C_7-C_{20})$phenylalkenyl, substituted $(C_7-C_{20})$phenylalkenyl, $(C_7-C_{20})$phenylalkynyl, substituted $(C_7-C_{20})$phenylalkynyl, $(C_1-C_6)$ alkoxy-$(C_2-C_6)$alkyl, phenoxy-$(C_2-C_6)$alkyl, substituted phenoxy-$(C_2-C_6)$alkyl, $(C_1-C_6)$alkoxy-$(C_2-C_6)$alkenyl, $(C_1-C_6)$alkoxy-$(C_2-C_6)$alkynyl, phenoxy-$(C_2-C_6)$alkenyl, substituted phenoxy-$(C_2-C_6)$alkenyl, phenoxy-$(C_2-C_6)$alkynyl, substituted phenoxy-$(C_2-C_6)$alkynyl, or $(C_7-C_{12})$phenylalkyl-$(C_7-C_{12})$phenylalkyl; $R_2$ is hydrogen, $(C_1-C_{15})$alkyl, cyclopentyl, cyclohexyl, $(C_3-C_{15})$alkenyl, phenyl, substituted phenyl, $(C_7-C_{20})$-phenylalkyl, substituted $(C_7-C_{20})$phenylalkyl or $(C_3-C_8)$-cycloalkyl-$(C_1-C_{15})$alkyl; or $R_1$ and $R_2$ together with the nitrogen atom to which they are attached form a pyrrolidinyl or piperidyl group which may be substituted by one $(C_1-C_6)$alkyl, phenyl or $(C_7-C_{20})$phenylalkyl; $R_3$ is $(C_1-C_6)$alkyl, phenyl, substituted phenyl, $(C_7-C_{20})$ phenylalkyl, substituted $(C_7-C_{20})$phenylalkyl, furyl, thienyl, furyl substituted by one $(C_1-C_3)$alkyl, thienyl substituted by one $C_1-C_3)$alkyl, $(C_1-C_6)$alkyl substituted with carbonyl, chloro, fluoro, bromo, iodo, trifluoromethyl, hydroxy or $(C_1-C_3)$alkoxy, $(C_2-C_6)$-alkenyl, $(C_2-C_6)$alkynyl, $(C_3-C_6)$cycloalkyl, $(C_1-C_{15})$-alkyl-$(C_3-C_8)$cycloalkyl, $(C_2-C_{15})$alkenyl-$(C_3-C_8)$-cycloalkyl, or $(C_2-C_{15})$alkynyl-$(C_3-C_8)$cycloalkyl; $R_4$ is hydrogen, $(C_1-C_6)$alkyl, phenyl substituted phenyl, $(C_7-C_{20})$phenylalkyl, or substituted $(C_7-C_{20})$phenylalkyl; and $R_6$ is hydrogen, $(C_1-C_{10})$ alkyl, $(C_1-C_{10})$-alkoxy, phenyl, substituted phenyl, $(C_7-C_{20})$phenylalkyl, substituted $(C_7-C_{20})$phenylalkyl, $(C_2-C_3)$alkylcarboxy, $-NR_8R_9$, wherein $R_8$ and $R_9$ are independently selected from the group consisting of $(C_1-C_{10})$alkyl, phenyl, substituted phenyl, $(C_7-C_{20})$phenylalkyl and substituted $(C_7-C_{20})$phenylalyl; wherein the phenyl moieties on said substituted phenyl, said substituted phenylalkyl, said substituted phenylalkenyl, said substituted phenylalkynyl, and said substituted phenoxy may be substituted by one or two moieties selected from the group consisting of fluoro, chloro, $(C_1-C_3)$alkyl, $(C_1-C_3)$-alkoxy and $CF_3$; with the proviso that when $R_1$ and $R_2$ are both hydrogen, $R_6$ cannot be methyl; a pharmaceutically acceptable acid addition salt thereof, or, when $R_6$ is $(C_2-C_3)$alkylcarboxy, a pharmaceutically acceptable base addition salt thereof.

3. A compound according to claim 2, wherein $R_2$ is hydrogen, $(C_1-C_{15})$alkyl, phenyl, substituted phenyl, $(C_7-C_{20})$phenylalkyl, or substituted $(C_7-C_{20})$phenylalkyl, wherein the phenyl moieties on said substituted phenyl and said substituted phenylalkyl are substituted by one or two moieties selected from the group consisting of chloro and $(C_1-C_3)$alkyl; $R_3$ is $(C_1-C_6)$alkyl, phenyl, or phenyl substituted by one or two moieties selected from the group consisting of fluoro, chloro, methyl, ethyl, methoxy, ethoxy, and $CF_3$; and $R_4$ is hydrogen, $(C_1-C_6)$alkyl, phenyl or phenyl substituted by one or two moieties selected from the group consisting of methyl and ethyl.

4. A compound according to claim 3, wherein $R_1$ is hydrogen and $R_2$ is other than hydrogen.

5. A compound according to claim 2, wherein $R^1$ is hydrogen; $R^2$ is $(C_7-C_{12})$phenylalkyl which may be substituted in the phenyl moiety by one or two moieties selected from the group consisting of fluoro, chloro, $(C_1-C_3)$alkyl, $(C_1-C_3)$alkoxy, and $CF_3$; and $R_3$ and $R_4$ are each methyl.

6. A compound according to claim 2, wherein $R^1$ is hydrogen: $R_2$ is $(C_8-C_9)$alkyl, $(C_9-C_{12})$phenylalkyl, $(C_9-C_{12})$p-chlorophenylalkyl or $(C_{10}-C_{13})$p-methylphenylalkyl; $R_3$ and $R_4$ are each methyl; and $R_6$ is $(C_1-C_6)$-alkyl or $(C_1-C_6)$alkoxy.

7. A compound according to claim 1, said compound being selected from the group consisting of 5-acetoxy-4,6-dimethyl-2-phenylhexylaminopyrimidine, 4,6-dimethyl-2-phenylhexylamino-5-(ethyloxyformyl)oxypyrimidine and the acid addition salts of the foregoing compounds.

8. A compound according to claim 2, said compound being selected from the group consisting of 5-benzoyloxy-4,6-dimethyl-2-phenylhexylaminopyrimidine; 4,6-dimethyl-2-phenylhexylamino-5-o-toluyloxypyrimidine: 5-caproyloxy-4,6-dimethyl-2-phenylhexylaminopyrimidine: 5-(oxo-(1-carboxy-5-phenylpentanel))-4,6-dimethyl-2-phenylhexylaminopyrimidine: 4,6-dimethyl-5-[p-N,N-diethylmethylamino)]benzoyloxy-2-phenylhexylaminopyrimidine: 4,6-dimethyl-2-phenylhexylamino-5-succinoyloxypyrimidine: 4,6-dimethyl-2-phenylhexylamino-5-propanoyloxypyrimidine: 4,6-dimethyl-2-phenylamino-5-(2-thienoyl)oxypyrimidine: 4,6-dimethyl-2-phenylhexylamino-5-(phenyloxyformyl)oxypyrimidine: 4,6-dimethyl-2-phenylhexylamino-5-(isobutyloxyformyl)oxypyrimidine; 5-(N,N-dimethylaminoformyl)oxy-4,6-dimethyl-2-phenylhexylaminopyrimidine; 5-(N,N-dimethylaminoformyl)oxy-4-isopropyl-6-methyl-2-phenylhexylaminopyrimidine; 4,6-dimethyl-5-oxo(1-carboxy-2,2-dimethylpropane)-2-phenylpentylaminopyrimidine; 4,6-dimethyl-2-phenylpentylamino-5-(isobutyloxyformyl)oxypyrimidine: 5-benzoyloxy- 4,6-dimethyl-2-phenylhexylaminopyrimidine; 5-(N,N-dimethylaminoformyl)oxy-4,6-dimethyl-2-phenylpentylaminopyrimidine; and the acid addition salts of the foregoing compounds.

9. A compound according to claim 1, where $R_2$ is hydrogen, $(C_1-C_{15})$alkyl, or $(C_7-C_{20})$phenylalkyl which may be substituted in the phenyl by one or two of chloro or $(C_1-C_3)$alkyl; $R_3$ is $(C_1-C_6)$alkyl, phenyl which may be substituted by one or two fluoro, chloro, methyl, ethyl, methoxy, ethoxy, or $CF_3$; and $R_4$ is hydrogen, $(C_1-C_6)$alkyl, phenyl or phenyl substituted by one or two methyl or ethyl.

10. A compound according to claim 1, with the provision that when $R_7$ is hydrogen and (1) $R_3$ and $R_4$ are each methyl, then $R_1$ and $R_2$ are not each hydrogen, or (2) $R_3$ and $R_4$ are each phenyl, then $R_1$ and $R_2$ are not each methyl.

11. A compound according to claim 9, wherein $R_7$ is hydrogen and (1) $R_3$ and $R_4$ are each methyl, then $R_1$ and $R_2$ are not each hydrogen, or (2) $R_3$ and $R_4$ are each phenyl, then $R_1$ and $R_2$ are not each methyl.

12. A compound according to claim 1, wherein $R_2$ is $(C_3-C_8)$cycloalkyl-$(C_1-C_{15})$alkyl.

13. A compound according to claim 9 wherein $R_2$ is $(C_3-C_8)$cycloalkyl-$(C_1-C_{15})$alkyl.

14. A compound according to claim 10 wherein $R_2$ is $(C_3-C_8)$cycloalkyl-$(C_1-C_{15})$alkyl.

15. A compound according to claim 11, wherein $R_2$ is $(C_3-C_8)$cycloalkyl-$(C_1-C_{15})$alkyl.

16. A compound of the formula

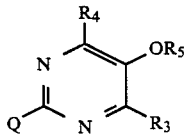

wherein Q is $SO_nR_{10}$, wherein n is an integer from 0 to 2; $R_3$ and $R_4$ are independently selected from the group consisting of hydrogen, $(C_1-C_6)$alkyl, phenyl, substituted phenyl, $(C_7-C_{20})$-phenylalkyl, substituted $(C_7-C_{20})$phenylalkyl, furyl, thienyl, furyl substituted by one $(C_1-C_3)$alkyl, thienyl substituted by one $(C_1-C_3)$alkyl, $(C_1-C_6)$alkyl substituted with carbonyl, chloro, fluoro, bromo, iodo, trifluoromethyl, hydroxy or alkoxy $(C_1-C_3)$, $(C_2-C_6)$alkenyl, $(C_2-C_6)$alkynyl, $(C_3-C_6)$cycloalkyl, $(C_1-C_{15})$alkyl -$(C_3-C_8)$cycloalkyl, $(C_2-C_{15})$alkenyl - $(C_3-C_8)$-cycloalkyl, or $(C_2-C_{15})$alkynyl-$(C_3-C_8)$cycloalkyl; $R_5$ is —$COR_6$ —$CH(CH_3)OCOOR_{11}$, —$CH_2OCOOR_{11}$ or $R_7$; $R_6$ is hydrogen, $(C_1-C_{10})$ alkyl, $(C_1-C_{10})$alkoxy, phenyl, substituted phenyl, $(C_7-C_{20})$-phenylalkyl, substituted $(C_7-C_{20})$phenylalkyl, $(C_2-C_3)$alkylcarboxy, —$NR_8R_9$, wherein $R_8$ and $R_9$ are independently selected from the group consisting of $(C_1-C_{10})$alkyl, phenyl, substituted phenyl, $(C_7-C_{20})$phenylalkyl and substituted $(C_7-C_{20})$phenylalkyl; $R_7$ is hydrogen or $(C_1-C_6)$alkyl; $R_{10}$ is $(C_5-C_{15})$alkyl, $(C_5-C_{15})$-alkenyl, phenyl, substituted phenyl, $(C_7-C_{20})$phenylalkyl, substituted $(C_7-C_{20})$phenylalkyl, $(C_7-C_{20})$phenylalkyl- $(C_7-C_{20})$-phenylalkyl, $(C_1-C_{17})$alkyl- $(C_3-C_8)$cycloalkyl, $(C_2-C_{17})$alkenyl-$(C_3-C_8)$cycloalkyl, $(C_2-C_{17})$alkynyl- $(C_3-C_8)$cycloalkyl, $C_5-C_{15})$-alkynyl, a heteroaryl containing group selected from heteroaryl$(C_1-C_{10})$alkyl, heteroaryl- $(C_1-C_{10})$alkenyl, and heteroaryl- $C_1-C_{10})$alkynyl, wherein the heteroaryl moiety is selected from the group consisting of thiophene, and furane, $(C_7-C_{20})$phenylalkynyl, substituted $(C_7-C_{20})$phenylalkynyl, $(C_1-C_6)$alkoxy- $(C_4-C_6)$alkyl, phenoxy $(C_2-C_6)$alkyl, substituted phenoxy- $(C_2-C_6)$alkyl, $(C_1-C_6)$alkoxy- $(C_3-C_6)$alkenyl, $(C_1-C_6)$alkoxy-$(C_3-C_6)$alkynyl, phenoxy- $(C_3-C_6)$alkenyl, substituted phenoxy- $(C_3-C_6)$alkenyl, phenoxy- $C_3-C_6$(alkynyl), or substituted phenoxy- $(C_3-C_6)$alkynyl; wherein the phenyl moieties on said substituted phenyl, said substituted phenylalkyl, said substituted phenylalkenyl, said substituted phenylalkylnyl, and said substituted phenoxy may be substituted by one or two moieties selected from the group consisting of fluoro, chloro, bromo, iodo, hydroxy, $(C_1-C_3)$alkyl, $(C_1-C_3)$alkoxy and $CF_3$; and $R_{11}$ is $(C_1-C_4)$alkyl; or a pharmaceutically acceptable acid addition salt thereof.

17. A compound according to claim 16, wherein n is 0 and $R_{10}$ is as defined in claim 1.

18. A compound according to claim 16, said compound being selected from the group consisting of 4,6-dimethyl-5-hydroxy-2-(n-heptyl)thiopyrimidine, 4,6 dimethyl-5-hydroxy-2-(n-nonyl)thiopyrimidine, 4,6-dimethyl-5-hydroxy-2-(p-chlorobenzyl)thiopyrimidine, 4,6-dimethyl-5-hydroxy-2-(p-methylbenzyl)-thiopyrimidine, 4,6 dimethyl-5-hydroxy-2-(5-phenyl-1-pentyl)thiopyrimidine, 4,6-dimethyl-5-hydroxy-2-benzylthiopyrimidine.

19. A compound of the formula

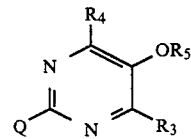

wherein Q is $R_1R_2N$— or $SO_nR_{10}$, wherein n is an integer from 0 to 2, $R_1$ is $(C_7-C_{20})$phenylalkenyl, substituted $(C_7-C_{20})$-phenylalkenyl $(C_7-C_{20})$phenylalkenyl, substituted $(C_7-C_{20})$-phenylalkynyl, $(C_1-C_6$ alkoxy) - $(C_2-C_6)$alkyl, phenoxy -$(C_2-C_6)$-alkyl, substituted phenoxy -$(C_2-C_6)$alkyl, $(C_1-C_6)$alkoxy- $(C_2-C_6)$alkenyl, $(C_2-C_6)$alkoxy -$(C_2-C_6)$alkynyl, phenoxy -$(C_2-C_6)$alkenyl, substituted phenoxy- $(C_2-C_6)$alkenyl, phenoxy -$(C_2-C_6)$alkynyl, substituted phenoxy- $(C_2-C_6)$alkynyl, or $(C_7\ C_{12})$phenylalkyl- $(C_7-C_{12})$phenylalkyl; $R_2$ is hydrogen, $(C_1-C_{15})$alkyl, cyclopentyl, cyclohexyl, $(C_3-C_{15})$alkenyl, phenyl, substituted phenyl, $(C_7-C_{20})$-phenylalkyl, substituted $(C_7-C_{20})$phenylalkyl or $(C_3-C_8)$cycloalkyl -$(C_1-C_{15})$alkyl; or $R_1$ and $R_2$ together with the nitrogen atom to which they are attached form a pyrrolidinyl or piperidyl group which may be substituted by one $(C_1-C_6)$alkyl, phenyl or $(C_7-C_{20})$ phenylalkyl; $R_3$ and $R_4$ are independently selected from the group consisting of hydrogen, $(C_1-C_6)$alkyl, phenyl substituted phenyl, $(C_7-C_{20})$-phenylalkyl, substituted $(C_7-C_{20})$phenylalkyl, furyl, thienyl, furyl substituted by one $(C_1-C_3)$ alkyl, thienyl substituted by one $(C_1-C_3)$alkyl, $(C_1-C_6)$alkyl substituted with carbonyl, chloro, fluoro, bromo, iodo, trifluoromethyl, hydroxy or alkoxy $(C_1-C_3)$, $(2-C_6)$alkenyl, $(2-C_6)$(alkynyl, $(C_3-C_6)$cycloalkyl, $(C_1-C_{15}$alkyl-$(C_3-C_8$ cycloalkyl, $(C_2-C_{15})$alkenyl - $(C_3-C_8)$-cycloalkyl, or $(C_2-C_{15})$alkynyl- $(C_3-C_8)$cycloalkyl; $R_5$ is -$COR_6$ —$CH(CH_3)OCOOR_{11}$, —$CH_2OCOOR_{11}$ or $R_7$; $R_6$ is hydrogen, $(C_1-C_{10})$ alkyl, $(C_1-C_{10})$alkoxy, phenyl, substituted phenyl, $(C_7-C_{20})$-phenylalkyl, substituted $(C_7-C_{20})$phenylalkyl, $(C_2-C_3)$-alkylcarboxy, —$NR_8R_9$, wherein $R_8$ and $R_9$ are independently selected from the group consisting of $(C_1-C_{10})$alkyl, phenyl, substituted phenyl, $(C_7-C_{20})$phenylalkyl and substituted $(C_7\ C_{20})$phenylalkyl; $R_7$ is hydrogen or $(C_1-C_6)$alkyl; $R_{10}$ is $(C_5-C_{15})$alkyl, $(C_5-C_{15})$alkenyl, phenyl, substituted phenyl, $(C_7-C_{20})$ phenylalkyl, substituted $(C_7-C_{20})$phenylalkyl, $(C_7-C_{20})$phenylalkyl- $(C_7-C_{20})$phenylalkyl, $(C_1-C_{17})$alkyl-$(C_3-C_8)$cycloalkyl, $(C_2-C_{17})$alkenyl-$(C_3-C_8)$cycloalkyl, $(C_2-C_{17})$alkynyl- $(c3-C_8)$cycloalkyl, $(C_5-C_{15})$alkynyl, a heteroaryl containing group selected from heteroaryl- $(C_1-C_{10})$-alkyl, heteroaryl-$(C_1-C_{10})$alkenyl, and heteroaryl$(C_1-C_{10})$alkynyl, wherein the hetero moiety is selected from the group consisting of thiophene, and furane, $(C_7-C_{20})$-phenylalkenyl substituted $(C_7-C_{20})$phenylalkyl, $(C_7-C_{20})$phenylalkynyl, substituted $(C_7-C_{20})$- phenylalkynyl, $(C_1-C_6)$alkoxy- $(C_4-C_6)$alkyl, phenoxy- $(C_2-C_6)$alkyl, substituted phenoxy- $(C_2-C_6)$alkyl, $(C_1-C_6)$alkoxy- $C_3-C_6)$alkenyl, $(C_1-C_{60})$-alkoxy $(C_3-C_6)$alkynyl, phenoxy- $(C_3-C_6)$alkenyl, substituted phenoxy- $(C_3-C_6)$alkenyl, phenoxy- $C_3-C_6$(alkynyl), or substituted phenoxy- $(C_3-C_6)$alkynyl; wherein the phenyl moieties on said substituted phenyl, said substituted phenylalkyl, said substituted phenylalkyl, said substituted phenylalkynyl, and said substituted phenoxy may be substituted by one or two moieties selected from the group consisting of fluoro, chloro, bromo, iodo, hydroxy, $(C_1-C_3)$alkyl, $(C_1-C_3)$alkoxy, and $CF_3$; $R_{11}$ is $(C_1-C_4)$alkyl; with the proviso that when Q is $R_1R_2N-$, $R_7$ is hydrogen and $R_3$ is $(C_1-C_6)$alkyl, then $R_4$ is not hydrogen; and with the proviso that when Q is $R_1R_2N-$, $R_3$ and $R_4$ are not both hydrogen; or a pharmaceutically acceptable acid addition salt thereof, or, when $R_6$ is $(C_2-C_3)$alkylcarboxy or $R_7$ is hydrogen, a pharmaceutically acceptable base addition salt thereof.

20. A compound according to any one of claims 16–19, wherein said addition salt is a phosphate addition salt.

21. A pharmaceutical composition for the treatment of pulmonary, asthmatic, allergic or inflammatory diseases which comprises an amount of a compound according to any one of claims 16–19 effective in treating at least one such disease and a pharmaceutically acceptable carrier.

22. A method for the treatment of pulmonary, asthmatic, allergic, psoriatic, or inflammatory disease which comprises administering to a mammal in need of such treatment a compound according to any one of claims 16–19 in an amount effective for the treatment of said disease.

23. A method of inhibiting leukotriene synthesis in a mammal comprising administering to a mammal in need of such treatment a compound according to any one of claims 16–19 in an amount effective to inhibit said synthesis.

* * * * *